United States Patent
Van Hijum et al.

(10) Patent No.: US 6,635,460 B1
(45) Date of Patent: Oct. 21, 2003

(54) FRUCTOSYLTRANSFERASES

(75) Inventors: Sacha Adrianus Fokke Taco Van Hijum, Groningen (NL); Gerritdina Hendrika Van Geel-Schutten, Driebergen-Rijsenburg (NL); Lubbert Dijkhuizen, Zuidlaren (NL); Hakim Rahaoui, Amersfoort (NL)

(73) Assignee: Nederlandse Organisatie voor Toegepast - Natuurwetenschappelijk Onderzoek TNO, Delft (NL)

( * ) Notice: Subject to any disclaimer, the term of this patent is extended or adjusted under 35 U.S.C. 154(b) by 0 days.

(21) Appl. No.: 09/604,958

(22) Filed: Jun. 28, 2000

(30) Foreign Application Priority Data

May 25, 2000 (EP) .............................. 00201872

(51) Int. Cl.[7] .............................. C12N 9/10; C12N 15/54
(52) U.S. Cl. ...................................... 435/193; 536/23.2
(58) Field of Search .......................... 435/193; 536/23.2

(56) References Cited

PUBLICATIONS

G.H. van Geel–Schutten et al. "Biochemical and Structural Characterization of the Glucan and Fructan Exoplysaccharides Synthesized by the Lactobacillus reuteri Wild–Type Strain and by Mutant Strains", Applied Environ. Microbiol. 65(7): 3008–3014. (Jul. 1.*

G.H. van Geel–Schutten et al. "Screening and Charcterization of Lactobacillus Strains Producing Large Amounts of Exopolysaccharides", Appl. Microbiol. Biotechnol. 50: 697–703. (1998).*

Shiroza et al. Sequence Analysis of the Streptococcus mutans Fructosyltransferase Gene and Flanking Regions. J. Bacteriology 170: 810–816. (1988).*

Tang et al. Isolation and Characterization of Levansucrase Encoding Gene From Bacillus amyloliquefaciens. Gene 96:89–93. (1990).*

* cited by examiner

*Primary Examiner*—Rebecca E. Prouty
(74) *Attorney, Agent, or Firm*—Young & Thompson

(57) ABSTRACT

The present invention describes two novel proteins having fructosyltransferase activity. Both enzymes are derived from lactobacilli, which are food-grade microorganisms with the Generally Recognized As Safe (GRAS) status. One of these proteins produces an inulin and fructo-oligosaccharides, while the other produces a levan. According to the invention lactobacilli capable of producing an inulin and/or a levan and/or fructo-oligosaccharides using one or both of the fructosyltransferases can be used as a probiotic or a symbiotic.

5 Claims, 9 Drawing Sheets

Fig 1 ( 1 )

```
  1 tacaatgggg tggcggaggt gaagaaacgg ggttacttct atgctagaac gcaaggaaca 19ftf>
    y n g   v a e   v k k r   g y f   y a r   t
    y n g   v a e   v n t e   r g a   n g g   i 61 taaaaaaatg tataaaagcg gtaaaaattg ggcagtcgtt acactctcga ctgctgcgct
  1        m  y k s  g k n  w a v v  t l s  t a a 121 ggtatttggt gcaacaactg taaatgcatc cgcggacaca aatattgaaa acaatgattc
 18 l v f g  a t t  v n a  s a d t  n i e  n n d 181 ttctactgta caagttacaa caggtgataa tgatattgct gttaaaagtg tgacacttgg
 38 s s t v  q v t  t g d  n d i a  v k s  v t l 241 tagtggtcaa gttagtgcag ctagtgatac gactattaga acttctgcta atgcaaatag
 58 g s g q  v s a  a s d  t t i r  t s a  n a n 301 tgcttcttct gccgctaata cacaaaattc taacagtcaa gtagcaagtt ctgctgcaat
 78 s a s s  a a n  t q n  s n s q  v a s  s a a 361 aacatcatct acaagttccg cagcttcatt aaataacaca gatagtaaag cggctcaaga
 98 i t s s  t s s  a a s  l n n t  d s k  a a q 421 aaatactaat acagccaaaa atgatgacac gcaaaaagct gcaccagcta acgaatcttc
118 e n t n  t a k  n d d  t q k a  a p a  n e s 481 tgaagctaaa aatgaaccag ctgtaaacgt taatgattct tcagctgcaa aaaatgatga
138 s e a k  n e p  a v n  v n d s  s a a  k n d 541 tcaacaatcc agtaaaaaga atactaccgc taagttaaac aaggatgctg aaaacgttgt
158 d q q s  s k k  n t t  a k l n  k d a  e n v 601 aaaaaaggcg ggaattgatc ctaacagttt aactgatgac cagattaaag cattaaataa
178 v k k a  g i d  p n s  l t d d  q i k  a l n
```

Fig 1 (2)

```
 661 gatgaacttc tcgaaagctg caaagtctgg tacacaaatg acttataatg atttccaaaa
 198 k  m  n  f    s  k  a    a  k  s    g  t  q  m    t  y  n  d    f  q 721 gattgctgat acgttaatca aacaagatgg tcggtacaca gttccattct ttaaagcaag  20ftfi <
 218 k  i  a  d  t  l  i  k  q  d  g  r  y  t    v  p  f    f  k  a 781 tgaaatcaaa aatatgcctg ccgctacaac taaagatgca caaactaata ctattgaacc
 238 s  e  i  k    n  m  p    a  a  t    k  d  a  q  t  n    t  i  e 841 tttagatgta tgggattcat ggccagttca agatgttcgg acaggacaag ttgctaattg  5ftf >
 258 p  l  d  v   w  d  s    w  p  v    q  d  v  r    t  g  q    v  a  n    8ftfi <

901 gaatggctat caacttgtca tcgcaatgat gggaattcca aaccaaaatg ataatcatat
 278 w  n  g  y  q  l  v    i  a  m    m  g  i  p    n  q  n    d  n  h 961 ctatctctta tataataagt atggtgataa tgaattaagt cattggaaga atgtaggtcc   7ftf >
 298 i  y  l  l   y  n  k   y  g  d  n   e  l  s   h  w  k   n  v  g 1021 aattttttggc tataattcta ccgcggtttc acaagaatgg tcaggatcag ctgttttgaa   7ftf >
 318 p  i  f  g  y  n  s   t  a  v   s  q  e  w    s  g  s    a  v  l    6ftfi <

1081 cagtgataac tctatccaat tatttatac aagggtagac acgtctgata acaataccaa
 338 n  s  d  n   s  i  q   l  f  y   t  r  v  d    t  s  d    n  n  t 1141 tcatcaaaaa attgctagcg ctactcttta tttaactgat aataatggaa atgtatcact    NheI
 358 n  h  q  k   i  a  s   a  t  l   y  l  t  d   n  n  g   n  v  s    AC1(i)<>

1201 cgctcaggta cgaaatgact atattgtatt tgaaggtgat ggctattact accaaactta   AC2(i)<>
 378 l  a  q  v   r  n  d   y  i  v   f  e  g  d   g  y  y   y  q  t 1261 tgatcaatgg aaagctacta acaaaggtgc cgataatatt gcaatgcgtg atgctcatgt
 398 y  d  q  w   k  a  t    n  k  g  a  d  n  i    a  m  r    d  a  h
```

Fig 1 ( 3 )

```
1321 aattgaagat ggtaatggtg atcggtacct tgttttTgaa gcaagtactg gtttggaaaa
 418 v  i  e  d  g  n  g  d  r  y  l  v  f  e  a  s  t  g  l  e 1381 ttatcaaggc gaggaccaaa tttataactg gttaaattat ggcggagatg acgcatttaa
 438 n  y  q  g  e  d  q  i  y  n  w  l  n  y  g  g  d  d  a  f 1441 tatcaagagc ttatttagaa ttcttTccaa tgatgatatt aagagtcggg caacttgggc
 458 n  i  k  s  l  f  r  i  l  s  n  d  d  i  k  s  r  a  t  w 1501 taatgcagct atcggtatcc tcaaactaaa taaggacgaa aagaatccta aggtggcaga
 478 a  n  a  a  i  g  i  l  k  l  n  k  d  e  k  n  p  k  v  a 1561 gttatactca ccattaattt ctgcaccaat ggtaagcgat gaaattgagc gaccaaatgt
 498 e  l  y  s  p  l  i  s  a  p  m  v  s  d  e  i  e  r  p  n 1621 agttaaatta ggtaataaat attacttatt tgccgctacc cgtttaaatc gaggaagtaa
 518 v  v  k  l  g  n  k  y  y  l  f  a  a  t  r  l  n  r  g  s 1681 tgatgatgct tggatgaatg ctaattatgc cgttggtgat aatgttgcaa tggtcggata
 538 n  d  d  a  w  m  n  a  n  y  a  v  g  d  n  v  a  m  v  g 1741 tgttgctgat agtctaactg gatcttataa gccattaaat gattctggag tagtcttgac
 558 y  v  a  d  s  l  t  g  s  y  k  p  l  n  d  s  g  v  v  l 1801 tgcttctgtt cctgcaaact ggcggacagc aacttattca tattatgctg tccccgttgc
 578 t  a  s  v  p  a  n  w  r  t  a  t  y  s  y  y  a  v  p  v 1861 cggaaaagat gaccaagtat tagttacttc atatatgact aatagaaatg gagtagcggg
 598 a  g  k  d  d  q  v  l  v  t  s  y  m  t  n  r  n  g  v  a 1921 taaaggaatg gattcaactt gggcaccgag tttcttacta caaattaacc cggataacac 12ftfi <
 618 g  k  g  m  d  s  t  w  a  p  s  f  l  l  q  i  n  p  d  n
```

Fig 1 ( 4 )

```
1981 aactactgtt ttagctaaaa tgactaatca aggggattgg atttgggatg attcaagcga
 638 t  t  v    l  a  k    m  t  n    q  g  d    w  i  w    d  s  s 2041 aaatcttgat atgattggtg atttagactc cgctgcttta cctggcgaac gtgataaacc
 658 e  n  l  d  m  i  g  d  l  d    s  a  a  l  p  g  e    r  d  k 2101 tgttgattgg gacttaattg gttatggatt aaaaccgcat gatcctgcta caccaaatga
 678 p  v  d  w  d  l  i  g  y  g  l  k  p  h  d  p  a  t  p  n 2161 tcctgaaacg ccaactacac cagaaacccc tgagacacct aatactccca aaacaccaaa
 698 d  p  e  t  p  t  t  p  e  t  p  e  t  p  n  t  p  k  t  p 2221 gactcctgaa aatcctggga cacctcaaac tcctaataca cctaatactc cggaaattcc
 718 k  t  p  e  n  p  g  t  p  q  t  p  n  t  p  n  t  p  e  i 2281 tttaactcca gaaacgccta agcaacctga aacccaaact aataatcgtt tgccacaaac
 738 p  l  t  p  e  t  p  k  q  p  e  t  q  t  n  n  r  l  p  q 2341 tggaaataat gccaataaag ccatgattgg cctaggtatg ggaacattgc ttagtatgtt
 758 t  g  n  n  a  n  k  a  m  i  g  l  g  m  g  t  l  l  s  m 2401 tggtcttgca gaaattaaca aacgtcgatt taactaaata ctttaaaata aaaccgctaa
 778 f  g  l  a  e  i  n  k  r  r  f  n  -

2461 gccttaaatt cagcttaacg gttttttatt ttaaaagttt ttattgtaaa aaagcgaatt 2521 atcattaata ctaatgcaat tgttgtaaga ccttacgaca gtagtaacaa tgaatttgcc 2581 catctttgtc gg                                                NheI
```

Fig 2

- Zymomonas mobilis SacB
- Zymomonas mobilis LevU
- Zymomonas mobilis SucE2
- Erwinia amylovora Lsc
- Acetobacter diazotrophicus LsdA
- Cynara scolymus Ss-1ft
- Hordeum vulgare SF-6ft
- Allium cepa F-6gft
- Bacillus stearothermophilus SurB
- Bacillus subtilis SacB
- Bacillus amyloliquefaciens SacB
- Lactobacillus reuteri FTFB
- Streptococcus salivarius Ftf
- Lactobacillus reuteri FTFA
- Streptococcus mutans SacB Distance 10%

Fig 3 ( 1 )

SEQ ID No. 2:

```
  1  aacaattaca acggtgttgc tgaagttaat actgaacgtc
 41  aagctaatgg tcaaattggc gtagatggaa aaattattag
 81  tgctaacagt aatacaacca gtggctcgac aaatcaagaa
121  tcatctgcta ctaacaatac tgaaaatgct gttgttaatg
161  aaagcaaaaa tactaacaat actgaaaatg ctgttgttaa
201  tgaaaacaaa aatactaaca atactgaaaa tgctgttgtt
241  aatgaaaaca aaatactaa caacacagaa aacgataata
281  gtcaattaaa gttaactaat aatgaacaac catcagccgc
321  tactcaagca aacttgaaga agctaaatcc tcaagctgct
361  aaggctgttc aaaatgccaa gattgatgcc ggtagtttaa
401  cagatgatca aattaatgaa ttaaataaga ttaacttctc
441  taagtctgct gaaaagggtg caaaattgac ctttaaggac
481  ttagagggga ttggtaatgc tattgttaag caagatccac
521  aatatgctat tccttattct aatgctaagg aaatcaagaa
561  tatgcctgca acatacactg tagatgccca aacaggtaag
601  atggctcatc ttgatgtctg ggactcttgg ccagtacaag
641  atcctgtcac aggttatgta tctaattaca tgggttatca
681  actagttatt gctatgatgg gtattccaaa ttcgccaact
721  ggagataatc atatctatct tctttacaac aagtatggtg
761  ataatgactt ttctcattgg cgcaatgcag gttcaatctt
```

Fig 3 (2)

```
 801  tggaactaaa gaaacaaatg tgttccaaga atggtcaggt
 841  tcagctattg taaatgatga tggtacaatt caactatttt
 881  tcacctcaaa tgatacgtct gattacaagt tgaatgatca
 921  acgccttgct accgcaacat taaaccttaa tgttgatgat
 961  aacggtgttt caatcaagag tgttgataat tatcaagttt
1001  tgtttgaagg tgatggattt cactaccaaa cttatgaaca
1041  attcgcaaac ggcaagatc gtgaaaatga tgattactgc
1081  ttacgtgacc cacacgttgt tcaattagaa aatggtgatc
1121  gttatcttgt attcgaagct aatactggga cagaagatta
1161  ccaaagtgac gaccaaattt ataattgggc taactatggt
1201  ggcgatgatg ccttcaatat taagagttcc ttcaagcttt
1241  tgaataataa gaaggatcgt gaattggctg gtttagctaa
1281  tggtgcactt ggtatcttaa agctcactaa caatcaaagt
1321  aagccaaagg ttgaagaagt atactcacca ttggtatcta
1361  ctttgatggc ttgcgatgag gtaag
```

The N-terminal sequence of FTFB (levansucrase):

(A) Q V E S N N Y N G V A E V N T E R Q A N G Q I (G) (V) (D).

Internal peptide sequences of FTFB (levansucrase):

5ftf

| | | | |
|---|---|---|---|
| B. amyloliquefaciens SacB | 80 | GLDVWDSWPLQNAD | 93 |
| B. subtilis SacB | 82 | GLDVWDSWPLQNAD | 95 |
| S. mutans SacB | 243 | DLDVWDSWPVQDAK | 256 |
| S. salivarius Ftf | 282 | EIDVWDSWPVQDAK | 295 |

:.**********:*:*.

6ftfi

| | | | |
|---|---|---|---|
| B. amyloliquefaciens SacB | 156 | QTQEWSGSATFTSDGK | 171 |
| B. subtilis SacB | 158 | QTQEWSGSATFTSDGK | 173 |
| S. mutans SacB | 312 | LTQEWSGSATVNEDGS | 327 |
| S. salivarius Ftf | 351 | DDQQWSGSATVNSDGS | 366 |

*.:****...:.

12ftfi

| | | | |
|---|---|---|---|
| B. amyloliquefaciens SacB | 440 | KATFGPSPLMN | 450 |
| B. subtilis SacB | 440 | QSTFAPSFLLN | 450 |
| S. mutans SacB | 609 | NSTWAPSFLIQ | 619 |
| S. salivarius Ftf | 655 | KSTWAPSFLIK | 665 |

::*:******::

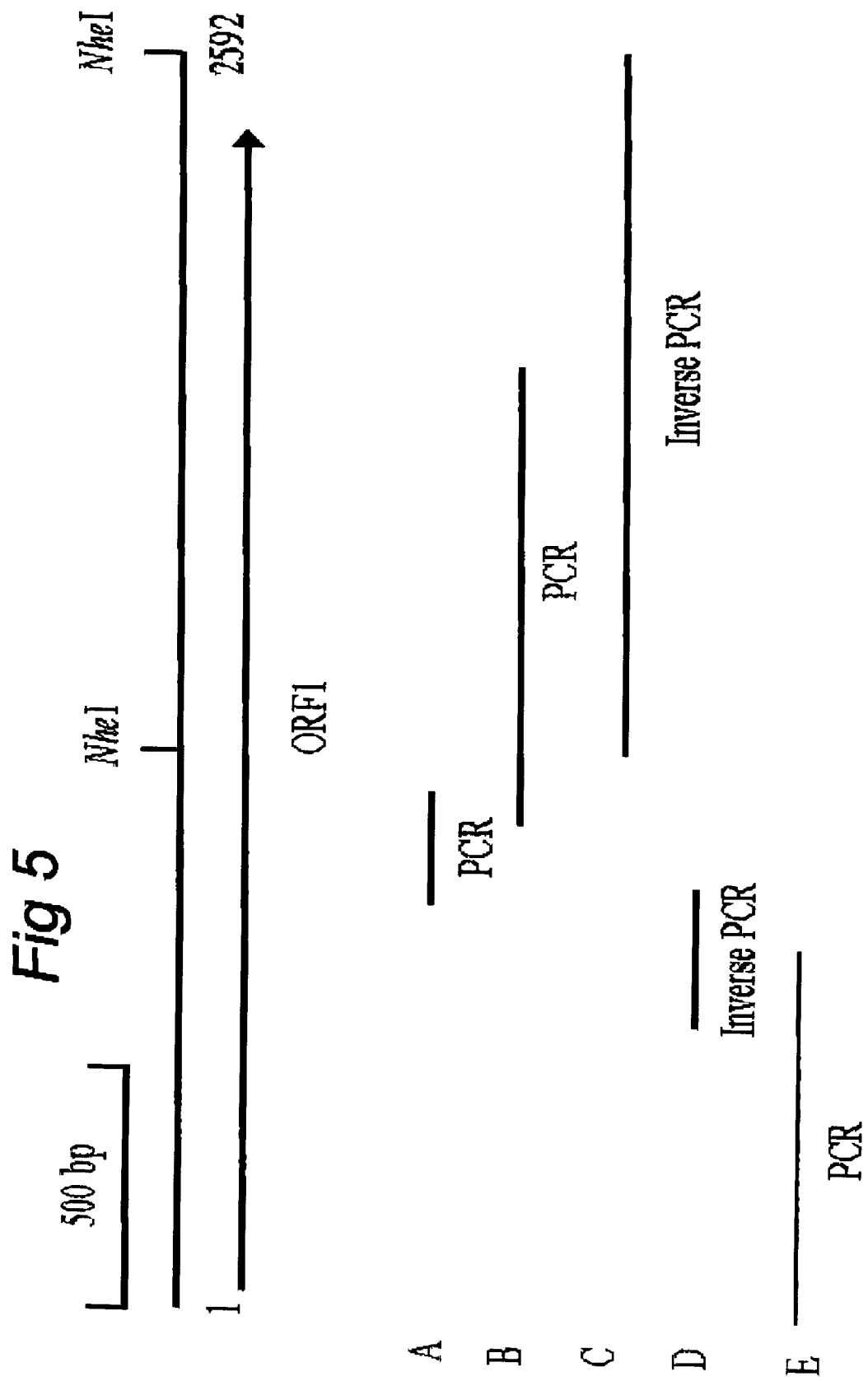

SEQUENCE LISTING

<160> NUMBER OF SEQ ID NOS: 50

<210> SEQ ID NO 1
<211> LENGTH: 789
<212> TYPE: PRT
<213> ORGANISM: Lactobacillus reuteri

<400> SEQUENCE: 1

```
Met Tyr Lys Ser Gly Lys Asn Trp Ala Val Val Thr Leu Ser Thr Ala
 1               5                  10                  15

Ala Leu Val Phe Gly Ala Thr Thr Val Asn Ala Ser Ala Asp Thr Asn
                20                  25                  30

Ile Glu Asn Asn Asp Ser Ser Thr Val Gln Val Thr Thr Gly Asp Asn
            35                  40                  45

Asp Ile Ala Val Lys Ser Val Thr Leu Gly Ser Gly Gln Val Ser Ala
        50                  55                  60

Ala Ser Asp Thr Thr Ile Arg Thr Ser Ala Asn Ala Asn Ser Ala Ser
 65                 70                  75                  80

Ser Ala Ala Asn Thr Gln Asn Ser Asn Ser Gln Val Ala Ser Ser Ala
                85                  90                  95

Ala Ile Thr Ser Ser Thr Ser Ser Ala Ala Ser Leu Asn Asn Thr Asp
                100                 105                 110

Ser Lys Ala Ala Gln Glu Asn Thr Asn Thr Ala Lys Asn Asp Asp Thr
            115                 120                 125

Gln Lys Ala Ala Pro Ala Asn Glu Ser Ser Glu Ala Lys Asn Glu Pro
        130                 135                 140

Ala Val Asn Val Asn Asp Ser Ser Ala Ala Lys Asn Asp Asp Gln Gln
145                 150                 155                 160

Ser Ser Lys Lys Asn Thr Thr Ala Lys Leu Asn Lys Asp Ala Glu Asn
                165                 170                 175

Val Val Lys Lys Ala Gly Ile Asp Pro Asn Ser Leu Thr Asp Asp Gln
                180                 185                 190

Ile Lys Ala Leu Asn Lys Met Asn Phe Ser Lys Ala Ala Lys Ser Gly
            195                 200                 205

Thr Gln Met Thr Tyr Asn Asp Phe Gln Lys Ile Ala Asp Thr Leu Ile
        210                 215                 220

Lys Gln Asp Gly Arg Tyr Thr Val Pro Phe Phe Lys Ala Ser Glu Ile
225                 230                 235                 240

Lys Asn Met Pro Ala Ala Thr Thr Lys Asp Ala Gln Thr Asn Thr Ile
                245                 250                 255

Glu Pro Leu Asp Val Trp Asp Ser Trp Pro Val Gln Asp Val Arg Thr
                260                 265                 270

Gly Gln Val Ala Asn Trp Asn Gly Tyr Gln Leu Val Ile Ala Met Thr
            275                 280                 285

Gly Ile Pro Asn Gln Asn Asp Asn His Ile Tyr Leu Leu Tyr Asn Lys
        290                 295                 300

Tyr Gly Asp Asn Glu Leu Ser His Trp Lys Asn Val Gly Pro Ile Phe
305                 310                 315                 320

Gly Tyr Asn Ser Thr Ala Val Ser Gln Glu Trp Ser Gly Ser Ala Val
                325                 330                 335

Leu Asn Ser Asp Asn Ser Ile Gln Leu Phe Tyr Thr Arg Val Asp Thr
                340                 345                 350

Ser Asp Asn Asn Thr Asn His Gln Lys Ile Ala Ser Ala Thr Leu Tyr
```

```
              355                 360                 365
Leu Thr Asp Asn Asn Gly Asn Val Ser Leu Ala Gln Val Arg Asn Asp
        370                 375                 380
Tyr Ile Val Phe Glu Gly Asp Gly Tyr Tyr Gln Thr Tyr Asp Gln
385                 390                 395                 400
Trp Lys Ala Thr Asn Lys Gly Ala Asp Asn Ile Ala Met Arg Asp Ala
                405                 410                 415
His Val Ile Glu Asp Gly Asn Gly Asp Arg Tyr Leu Val Phe Glu Ala
                420                 425                 430
Ser Thr Gly Leu Glu Asn Tyr Gln Gly Glu Asp Gln Ile Tyr Asn Trp
                435                 440                 445
Leu Asn Tyr Gly Gly Asp Asp Ala Phe Asn Ile Lys Ser Leu Phe Arg
        450                 455                 460
Ile Leu Ser Asn Asp Asp Ile Lys Ser Arg Ala Thr Trp Ala Asn Ala
465                 470                 475                 480
Ala Ile Gly Ile Leu Lys Leu Asn Lys Asp Lys Asn Pro Lys Val
                485                 490                 495
Ala Glu Leu Tyr Ser Pro Leu Ile Ser Ala Pro Met Val Ser Asp Glu
                500                 505                 510
Ile Glu Arg Pro Asn Val Val Lys Leu Gly Asn Lys Tyr Tyr Leu Phe
                515                 520                 525
Ala Ala Thr Arg Leu Asn Arg Gly Ser Asn Asp Asp Ala Trp Met Asn
        530                 535                 540
Ala Asn Tyr Ala Val Gly Asp Asn Val Ala Met Val Gly Tyr Val Ala
545                 550                 555                 560
Asp Ser Leu Thr Gly Ser Tyr Lys Pro Leu Asn Asp Ser Gly Val Val
                565                 570                 575
Leu Thr Ala Ser Val Pro Ala Asn Trp Arg Thr Ala Thr Tyr Ser Tyr
                580                 585                 590
Tyr Ala Val Pro Val Ala Gly Lys Asp Asp Gln Val Leu Val Thr Ser
                595                 600                 605
Tyr Met Thr Asn Arg Asn Gly Val Ala Gly Lys Gly Met Asp Ser Thr
        610                 615                 620
Trp Ala Pro Ser Phe Leu Leu Gln Ile Asn Pro Asp Asn Thr Thr Thr
625                 630                 635                 640
Val Leu Ala Lys Met Thr Asn Gln Gly Asp Trp Ile Trp Asp Asp Ser
                645                 650                 655
Ser Glu Asn Leu Asp Met Ile Gly Asp Leu Asp Ser Ala Ala Leu Pro
                660                 665                 670
Gly Glu Arg Asp Lys Pro Val Asp Trp Asp Leu Ile Gly Tyr Gly Leu
                675                 680                 685
Lys Pro His Asp Pro Ala Thr Pro Asn Asp Pro Glu Thr Pro Thr Thr
        690                 695                 700
Pro Glu Thr Pro Glu Thr Pro Asn Thr Pro Lys Thr Pro Lys Thr Pro
705                 710                 715                 720
Glu Asn Pro Gly Thr Pro Gln Thr Pro Asn Thr Pro Asn Thr Pro Glu
                725                 730                 735
Ile Pro Leu Thr Pro Glu Thr Pro Lys Gln Pro Glu Thr Gln Thr Asn
                740                 745                 750
Asn Arg Leu Pro Gln Thr Gly Asn Asn Ala Asn Lys Ala Met Ile Gly
        755                 760                 765
Leu Gly Met Gly Thr Leu Leu Ser Met Phe Gly Leu Ala Glu Ile Asn
        770                 775                 780
```

Lys Arg Arg Phe Asn
785

<210> SEQ ID NO 2
<211> LENGTH: 1385
<212> TYPE: DNA
<213> ORGANISM: Lactobacillus reuteri

<400> SEQUENCE: 2

| | | | | |
|---|---|---|---|---|
| aacaattaca | acggtgttgc | tgaagttaat | actgaacgtc | aagctaatgg tcaaattggc | 60 |
| gtagatggaa | aaattattag | tgctaacagt | aatacaacca | gtggctcgac aaatcaagaa | 120 |
| tcatctgcta | ctaacaatac | tgaaaatgct | gttgttaatg | aaagcaaaaa tactaacaat | 180 |
| actgaaaatg | ctgttgttaa | tgaaaacaaa | aatactaaca | atactgaaaa tgctgttgtt | 240 |
| aatgaaaaca | aaaatactaa | caacacagaa | acgataata | gtcaattaaa gttaactaat | 300 |
| aatgaacaac | catcagccgc | tactcaagca | aacttgaaga | agctaaatcc tcaagctgct | 360 |
| aaggctgttc | aaaatgccaa | gattgatgcc | ggtagtttaa | cagatgatca aattaatgaa | 420 |
| ttaaataaga | ttaacttctc | taagtctgct | gaaaagggtg | caaaattgac ctttaaggac | 480 |
| ttagagggga | ttggtaatgc | tattgttaag | caagatccac | aatatgctat tccttattct | 540 |
| aatgctaagg | aaatcaagaa | tatgcctgca | acatacactg | tagatgccca acaggtaag | 600 |
| atggctcatc | ttgatgtctg | ggactcttgg | ccagtacaag | atcctgtcac aggttatgta | 660 |
| tctaattaca | tgggttatca | actagttatt | gctatgatgg | tattccaaa ttcgccaact | 720 |
| ggagataatc | atatctatct | tctttacaac | aagtatggtg | ataatgactt ttctcattgg | 780 |
| cgcaatgcag | gttcaatctt | tggaactaaa | gaaacaaatg | tgttccaaga atggtcaggt | 840 |
| tcagctattg | taaatgatga | tggtacaatt | caactatttt | tcacctcaaa tgatacgtct | 900 |
| gattacaagt | tgaatgatca | acgccttgct | accgcaacat | aaaccttaa tgttgatgat | 960 |
| aacggtgttt | caatcaagag | tgttgataat | tatcaagttt | tgtttgaagg tgatggattt | 1020 |
| cactaccaaa | cttatgaaca | attcgcaaac | ggcaaagatc | tgaaaatga tgattactgc | 1080 |
| ttacgtgacc | cacacgttgt | tcaattagaa | aatggtgatc | gttatcttgt attcgaagct | 1140 |
| aatactggga | cagaagatta | ccaaagtgac | gaccaaattt | ataattgggc taactatggt | 1200 |
| ggcgatgatg | ccttcaatat | taagagttcc | ttcaagcttt | tgaataataa gaaggatcgt | 1260 |
| gaattggctg | gttagctaa | tggtgcactt | ggtatcttaa | agctcactaa caatcaaagt | 1320 |
| aagccaaagg | ttgaagaagt | atactcacca | ttggtatcta | ctttgatggc ttgcgatgag | 1380 |
| gtaag | | | | | 1385 |

<210> SEQ ID NO 3
<211> LENGTH: 2592
<212> TYPE: DNA
<213> ORGANISM: Lactobacillus reuteri
<220> FEATURE:
<221> NAME/KEY: CDS
<222> LOCATION: (68)..(2434)

<400> SEQUENCE: 3

| | | | | |
|---|---|---|---|---|
| tacaatgggg | tggcggaggt | gaagaaacgg | ggttacttct | atgctagaac gcaaggaaca | 60 |

| taaaaaa | atg | tat | aaa | agc | ggt | aaa | aat | tgg | gca | gtc | gtt | aca | ctc | tcg | 109 |
| | Met | Tyr | Lys | Ser | Gly | Lys | Asn | Trp | Ala | Val | Val | Thr | Leu | Ser | |
| | 1 | | | 5 | | | | | 10 | | | | | 15 | |

| act | gct | gcg | ctg | gta | ttt | ggt | gca | aca | act | gta | aat | gca | tcc | gcg | gac | 157 |
| Thr | Ala | Ala | Leu | Val | Phe | Gly | Ala | Thr | Thr | Val | Asn | Ala | Ser | Ala | Asp |

|          |     |     |     | 15  |     |     |     |     | 20  |     |     |     |     | 25  |     |     |     |     | 30  |      |
|----------|-----|-----|-----|-----|-----|-----|-----|-----|-----|-----|-----|-----|-----|-----|-----|-----|-----|-----|-----|------|
| aca | aat | att | gaa | aac | aat | gat | tct | tct | act | gta | caa | gtt | aca | aca | ggt | | | | | 205 |
| Thr | Asn | Ile | Glu | Asn | Asn | Asp | Ser | Ser | Thr | Val | Gln | Val | Thr | Thr | Gly | | | | | |
| | | | | | 35 | | | | | 40 | | | | | 45 | | | | | |

| gat | aat | gat | att | gct | gtt | aaa | agt | gtg | aca | ctt | ggt | agt | ggt | caa | gtt | 253 |
|---|---|---|---|---|---|---|---|---|---|---|---|---|---|---|---|---|
| Asp | Asn | Asp | Ile | Ala | Val | Lys | Ser | Val | Thr | Leu | Gly | Ser | Gly | Gln | Val | |
| | | 50 | | | | | 55 | | | | | 60 | | | | |

| agt | gca | gct | agt | gat | acg | act | att | aga | act | tct | gct | aat | gca | aat | agt | 301 |
|---|---|---|---|---|---|---|---|---|---|---|---|---|---|---|---|---|
| Ser | Ala | Ala | Ser | Asp | Thr | Thr | Ile | Arg | Thr | Ser | Ala | Asn | Ala | Asn | Ser | |
| | 65 | | | | | 70 | | | | | 75 | | | | | |

| gct | tct | tct | gcc | gct | aat | aca | caa | aat | tct | aac | agt | caa | gta | gca | agt | 349 |
|---|---|---|---|---|---|---|---|---|---|---|---|---|---|---|---|---|
| Ala | Ser | Ser | Ala | Ala | Asn | Thr | Gln | Asn | Ser | Asn | Ser | Gln | Val | Ala | Ser | |
| | | 80 | | | | | 85 | | | | | 90 | | | | |

| tct | gct | gca | ata | aca | tca | tct | aca | agt | tcc | gca | gct | tca | tta | aat | aac | 397 |
|---|---|---|---|---|---|---|---|---|---|---|---|---|---|---|---|---|
| Ser | Ala | Ala | Ile | Thr | Ser | Ser | Thr | Ser | Ser | Ala | Ala | Ser | Leu | Asn | Asn | |
| 95 | | | | | 100 | | | | | 105 | | | | | 110 | |

| aca | gat | agt | aaa | gcg | gct | caa | gaa | aat | act | aat | aca | gcc | aaa | aat | gat | 445 |
|---|---|---|---|---|---|---|---|---|---|---|---|---|---|---|---|---|
| Thr | Asp | Ser | Lys | Ala | Ala | Gln | Glu | Asn | Thr | Asn | Thr | Ala | Lys | Asn | Asp | |
| | | | 115 | | | | | 120 | | | | | 125 | | | |

| gac | acg | caa | aaa | gct | gca | cca | gct | aac | gaa | tct | tct | gaa | gct | aaa | aat | 493 |
|---|---|---|---|---|---|---|---|---|---|---|---|---|---|---|---|---|
| Asp | Thr | Gln | Lys | Ala | Ala | Pro | Ala | Asn | Glu | Ser | Ser | Glu | Ala | Lys | Asn | |
| | | 130 | | | | | 135 | | | | | 140 | | | | |

| gaa | cca | gct | gta | aac | gtt | aat | gat | tct | tca | gct | gca | aaa | aat | gat | gat | 541 |
|---|---|---|---|---|---|---|---|---|---|---|---|---|---|---|---|---|
| Glu | Pro | Ala | Val | Asn | Val | Asn | Asp | Ser | Ser | Ala | Ala | Lys | Asn | Asp | Asp | |
| | 145 | | | | | 150 | | | | | 155 | | | | | |

| caa | caa | tcc | agt | aaa | aag | aat | act | acc | gct | aag | tta | aac | aag | gat | gct | 589 |
|---|---|---|---|---|---|---|---|---|---|---|---|---|---|---|---|---|
| Gln | Gln | Ser | Ser | Lys | Lys | Asn | Thr | Thr | Ala | Lys | Leu | Asn | Lys | Asp | Ala | |
| 160 | | | | | 165 | | | | | 170 | | | | | | |

| gaa | aac | gtt | gta | aaa | aag | gcg | gga | att | gat | cct | aac | agt | tta | act | gat | 637 |
|---|---|---|---|---|---|---|---|---|---|---|---|---|---|---|---|---|
| Glu | Asn | Val | Val | Lys | Lys | Ala | Gly | Ile | Asp | Pro | Asn | Ser | Leu | Thr | Asp | |
| 175 | | | | | 180 | | | | | 185 | | | | | 190 | |

| gac | cag | att | aaa | gca | tta | aat | aag | atg | aac | ttc | tcg | aaa | gct | gca | aag | 685 |
|---|---|---|---|---|---|---|---|---|---|---|---|---|---|---|---|---|
| Asp | Gln | Ile | Lys | Ala | Leu | Asn | Lys | Met | Asn | Phe | Ser | Lys | Ala | Ala | Lys | |
| | | | 195 | | | | | 200 | | | | | 205 | | | |

| tct | ggt | aca | caa | atg | act | tat | aat | gat | ttc | caa | aag | att | gct | gat | acg | 733 |
|---|---|---|---|---|---|---|---|---|---|---|---|---|---|---|---|---|
| Ser | Gly | Thr | Gln | Met | Thr | Tyr | Asn | Asp | Phe | Gln | Lys | Ile | Ala | Asp | Thr | |
| | | 210 | | | | | 215 | | | | | 220 | | | | |

| tta | atc | aaa | caa | gat | ggt | cgg | tac | aca | gtt | cca | ttc | ttt | aaa | gca | agt | 781 |
|---|---|---|---|---|---|---|---|---|---|---|---|---|---|---|---|---|
| Leu | Ile | Lys | Gln | Asp | Gly | Arg | Tyr | Thr | Val | Pro | Phe | Phe | Lys | Ala | Ser | |
| | 225 | | | | | 230 | | | | | 235 | | | | | |

| gaa | atc | aaa | aat | atg | cct | gcc | gct | aca | act | aaa | gat | gca | caa | act | aat | 829 |
|---|---|---|---|---|---|---|---|---|---|---|---|---|---|---|---|---|
| Glu | Ile | Lys | Asn | Met | Pro | Ala | Ala | Thr | Thr | Lys | Asp | Ala | Gln | Thr | Asn | |
| | 240 | | | | | 245 | | | | | 250 | | | | | |

| act | att | gaa | cct | tta | gat | gta | tgg | gat | tca | tgg | cca | gtt | caa | gat | gtt | 877 |
|---|---|---|---|---|---|---|---|---|---|---|---|---|---|---|---|---|
| Thr | Ile | Glu | Pro | Leu | Asp | Val | Trp | Asp | Ser | Trp | Pro | Val | Gln | Asp | Val | |
| 255 | | | | | 260 | | | | | 265 | | | | | 270 | |

| cgg | aca | gga | caa | gtt | gct | aat | tgg | aat | ggc | tat | caa | ctt | gtc | atc | gca | 925 |
|---|---|---|---|---|---|---|---|---|---|---|---|---|---|---|---|---|
| Arg | Thr | Gly | Gln | Val | Ala | Asn | Trp | Asn | Gly | Tyr | Gln | Leu | Val | Ile | Ala | |
| | | | 275 | | | | | 280 | | | | | 285 | | | |

| atg | acg | gga | att | cca | aac | caa | aat | gat | aat | cat | atc | tat | ctc | tta | tat | 973 |
|---|---|---|---|---|---|---|---|---|---|---|---|---|---|---|---|---|
| Met | Thr | Gly | Ile | Pro | Asn | Gln | Asn | Asp | Asn | His | Ile | Tyr | Leu | Leu | Tyr | |
| | | 290 | | | | | 295 | | | | | 300 | | | | |

| aat | aag | tat | ggt | gat | aat | gaa | tta | agt | cat | tgg | aag | aat | gta | ggt | cca | 1021 |
|---|---|---|---|---|---|---|---|---|---|---|---|---|---|---|---|---|
| Asn | Lys | Tyr | Gly | Asp | Asn | Glu | Leu | Ser | His | Trp | Lys | Asn | Val | Gly | Pro | |
| | | 305 | | | | | 310 | | | | | 315 | | | | |

| att | ttt | ggc | tat | aat | tct | acc | gcg | gtt | tca | caa | gaa | tgg | tca | gga | tca | 1069 |
|---|---|---|---|---|---|---|---|---|---|---|---|---|---|---|---|---|
| Ile | Phe | Gly | Tyr | Asn | Ser | Thr | Ala | Val | Ser | Gln | Glu | Trp | Ser | Gly | Ser | |
| | 320 | | | | | 325 | | | | | 330 | | | | | |

| gct | gtt | ttg | aac | agt | gat | aac | tct | atc | caa | tta | ttt | tat | aca | agg | gta | 1117 |
|---|---|---|---|---|---|---|---|---|---|---|---|---|---|---|---|---|

```
Ala Val Leu Asn Ser Asp Asn Ser Ile Gln Leu Phe Tyr Thr Arg Val
335                 340                 345                 350 gac acg tct gat aac aat acc aat cat caa aaa att gct agc gct act      1165
Asp Thr Ser Asp Asn Asn Thr Asn His Gln Lys Ile Ala Ser Ala Thr
                    355                 360                 365 ctt tat tta act gat aat aat gga aat gta tca ctc gct cag gta cga      1213
Leu Tyr Leu Thr Asp Asn Asn Gly Asn Val Ser Leu Ala Gln Val Arg
                370                 375                 380 aat gac tat att gta ttt gaa ggt gat ggc tat tac tac caa act tat      1261
Asn Asp Tyr Ile Val Phe Glu Gly Asp Gly Tyr Tyr Tyr Gln Thr Tyr
            385                 390                 395 gat caa tgg aaa gct act aac aaa ggt gcc gat aat att gca atg cgt      1309
Asp Gln Trp Lys Ala Thr Asn Lys Gly Ala Asp Asn Ile Ala Met Arg
        400                 405                 410 gat gct cat gta att gaa gat ggt aat ggt gat cgg tac ctt gtt ttt      1357
Asp Ala His Val Ile Glu Asp Gly Asn Gly Asp Arg Tyr Leu Val Phe
415                 420                 425                 430 gaa gca agt act ggt ttg gaa aat tat caa ggc gag gac caa att tat      1405
Glu Ala Ser Thr Gly Leu Glu Asn Tyr Gln Gly Glu Asp Gln Ile Tyr
                435                 440                 445 aac tgg tta aat tat ggc gga gat gac gca ttt aat atc aag agc tta      1453
Asn Trp Leu Asn Tyr Gly Gly Asp Asp Ala Phe Asn Ile Lys Ser Leu
            450                 455                 460 ttt aga att ctt tcc aat gat gat att aag agt cgg gca act tgg gct      1501
Phe Arg Ile Leu Ser Asn Asp Asp Ile Lys Ser Arg Ala Thr Trp Ala
        465                 470                 475 aat gca gct atc ggt atc ctc aaa cta aat aag gac gaa aag aat cct      1549
Asn Ala Ala Ile Gly Ile Leu Lys Leu Asn Lys Asp Glu Lys Asn Pro
480                 485                 490 aag gtg gca gag tta tac tca cca tta att tct gca cca atg gta agc      1597
Lys Val Ala Glu Leu Tyr Ser Pro Leu Ile Ser Ala Pro Met Val Ser
495                 500                 505                 510 gat gaa att gag cga cca aat gta gtt aaa tta ggt aat aaa tat tac      1645
Asp Glu Ile Glu Arg Pro Asn Val Val Lys Leu Gly Asn Lys Tyr Tyr
                515                 520                 525 tta ttt gcc gct acc cgt tta aat cga gga agt aat gat gat gct tgg      1693
Leu Phe Ala Ala Thr Arg Leu Asn Arg Gly Ser Asn Asp Asp Ala Trp
            530                 535                 540 atg aat gct aat tat gcc gtt ggt gat aat gtt gca atg gtc gga tat      1741
Met Asn Ala Asn Tyr Ala Val Gly Asp Asn Val Ala Met Val Gly Tyr
        545                 550                 555 gtt gct gat agt cta act gga tct tat aag cca tta aat gat tct gga      1789
Val Ala Asp Ser Leu Thr Gly Ser Tyr Lys Pro Leu Asn Asp Ser Gly
560                 565                 570 gta gtc ttg act gct tct gtt cct gca aac tgg cgg aca gca act tat      1837
Val Val Leu Thr Ala Ser Val Pro Ala Asn Trp Arg Thr Ala Thr Tyr
575                 580                 585                 590 tca tat tat gct gtc ccc gtt gcc gga aaa gat gac caa gta tta gtt      1885
Ser Tyr Tyr Ala Val Pro Val Ala Gly Lys Asp Asp Gln Val Leu Val
                595                 600                 605 act tca tat atg act aat aga aat gga gta gcg ggt aaa gga atg gat      1933
Thr Ser Tyr Met Thr Asn Arg Asn Gly Val Ala Gly Lys Gly Met Asp
            610                 615                 620 tca act tgg gca ccg agt ttc tta cta caa att aac ccg gat aac aca      1981
Ser Thr Trp Ala Pro Ser Phe Leu Leu Gln Ile Asn Pro Asp Asn Thr
        625                 630                 635 act act gtt tta gct aaa atg act aat caa ggg gat tgg att tgg gat      2029
Thr Thr Val Leu Ala Lys Met Thr Asn Gln Gly Asp Trp Ile Trp Asp
640                 645                 650
```

```
gat tca agc gaa aat ctt gat atg att ggt gat tta gac tcc gct gct    2077
Asp Ser Ser Glu Asn Leu Asp Met Ile Gly Asp Leu Asp Ser Ala Ala
655                 660                 665                 670 tta cct ggc gaa cgt gat aaa cct gtt gat tgg gac tta att ggt tat    2125
Leu Pro Gly Glu Arg Asp Lys Pro Val Asp Trp Asp Leu Ile Gly Tyr
            675                 680                 685 gga tta aaa ccg cat gat cct gct aca cca aat gat cct gaa acg cca    2173
Gly Leu Lys Pro His Asp Pro Ala Thr Pro Asn Asp Pro Glu Thr Pro
        690                 695                 700 act aca cca gaa acc cct gag aca cct aat act ccc aaa aca cca aag    2221
Thr Thr Pro Glu Thr Pro Glu Thr Pro Asn Thr Pro Lys Thr Pro Lys
    705                 710                 715 act cct gaa aat cct ggg aca cct caa act cct aat aca cct aat act    2269
Thr Pro Glu Asn Pro Gly Thr Pro Gln Thr Pro Asn Thr Pro Asn Thr
720                 725                 730 ccg gaa att cct tta act cca gaa acg cct aag caa cct gaa acc caa    2317
Pro Glu Ile Pro Leu Thr Pro Glu Thr Pro Lys Gln Pro Glu Thr Gln
735                 740                 745                 750 act aat aat cgt ttg cca caa act gga aat aat gcc aat aaa gcc atg    2365
Thr Asn Asn Arg Leu Pro Gln Thr Gly Asn Asn Ala Asn Lys Ala Met
                755                 760                 765 att ggc cta ggt atg gga aca ttg ctt agt atg ttt ggt ctt gca gaa    2413
Ile Gly Leu Gly Met Gly Thr Leu Leu Ser Met Phe Gly Leu Ala Glu
            770                 775                 780 att aac aaa cgt cga ttt aac taaatacttt aaaataaaac cgctaagcct       2464
Ile Asn Lys Arg Arg Phe Asn
                785 taaattcagc ttaacggttt tttattttaa aagttttat tgtaaaaaag cgaattatca   2524 ttaatactaa tgcaattgtt gtaagacctt acgacagtag taacaatgaa tttgcccatc  2584 tttgtcgg                                                          2592

<210> SEQ ID NO 4
<211> LENGTH: 17
<212> TYPE: PRT
<213> ORGANISM: Lactobacillus reuteri

<400> SEQUENCE: 4

Tyr Asn Gly Val Ala Glu Val Lys Lys Arg Gly Tyr Phe Tyr Ala Arg
 1               5                  10                  15
Thr

<210> SEQ ID NO 5
<211> LENGTH: 17
<212> TYPE: PRT
<213> ORGANISM: Lactobacillus reuteri

<400> SEQUENCE: 5

Tyr Asn Gly Val Ala Glu Val Asn Thr Glu Arg Gln Ala Asn Gly Gln
 1               5                  10                  15
Ile

<210> SEQ ID NO 6
<211> LENGTH: 27
<212> TYPE: PRT
<213> ORGANISM: Lactobacillus reuteri

<400> SEQUENCE: 6

Ala Gln Val Glu Ser Asn Asn Tyr Asn Gly Val Ala Glu Val Asn Thr
 1               5                  10                  15
```

Glu Arg Gln Ala Asn Gly Gln Ile Gly Val Asp
            20                  25

<210> SEQ ID NO 7
<211> LENGTH: 16
<212> TYPE: PRT
<213> ORGANISM: Lactobacillus reuteri

<400> SEQUENCE: 7

Met Ala His Leu Asp Val Trp Asp Ser Trp Pro Val Gln Asp Pro Val
1               5                   10                  15

<210> SEQ ID NO 8
<211> LENGTH: 9
<212> TYPE: PRT
<213> ORGANISM: Lactobacillus reuteri

<400> SEQUENCE: 8

Asn Ala Gly Ser Ile Phe Gly Thr Lys
1               5

<210> SEQ ID NO 9
<211> LENGTH: 19
<212> TYPE: PRT
<213> ORGANISM: Lactobacillus reuteri

<400> SEQUENCE: 9

Val Glu Glu Val Tyr Ser Pro Lys Val Ser Thr Leu Met Ala Ser Asp
1               5                   10                  15

Glu Val Glu

<210> SEQ ID NO 10
<211> LENGTH: 14
<212> TYPE: PRT
<213> ORGANISM: Bacillus amyloliquefaciens

<400> SEQUENCE: 10

Gly Leu Asp Val Trp Asp Ser Trp Pro Leu Gln Asn Ala Asp
1               5                   10

<210> SEQ ID NO 11
<211> LENGTH: 14
<212> TYPE: PRT
<213> ORGANISM: Bacillus subtilis

<400> SEQUENCE: 11

Gly Leu Asp Val Trp Asp Ser Trp Pro Leu Gln Asn Ala Asp
1               5                   10

<210> SEQ ID NO 12
<211> LENGTH: 14
<212> TYPE: PRT
<213> ORGANISM: Streptococcus mutans

<400> SEQUENCE: 12

Asp Leu Asp Val Trp Asp Ser Trp Pro Val Gln Asp Ala Lys
1               5                   10

<210> SEQ ID NO 13
<211> LENGTH: 14
<212> TYPE: PRT
<213> ORGANISM: Streptococcus salivarius

<400> SEQUENCE: 13

Glu Ile Asp Val Trp Asp Ser Trp Pro Val Gln Asp Ala Lys
1               5                   10

<210> SEQ ID NO 14
<211> LENGTH: 16
<212> TYPE: PRT
<213> ORGANISM: Bacillus amyloliquefaciens

<400> SEQUENCE: 14

Gln Thr Gln Glu Trp Ser Gly Ser Ala Thr Phe Thr Ser Asp Gly Lys
1               5                   10                  15

<210> SEQ ID NO 15
<211> LENGTH: 16
<212> TYPE: PRT
<213> ORGANISM: Bacillus subtilis

<400> SEQUENCE: 15

Gln Thr Gln Glu Trp Ser Gly Ser Ala Thr Phe Thr Ser Asp Gly Lys
1               5                   10                  15

<210> SEQ ID NO 16
<211> LENGTH: 16
<212> TYPE: PRT
<213> ORGANISM: Streptococcus mutans

<400> SEQUENCE: 16

Leu Thr Gln Glu Trp Ser Gly Ser Ala Thr Val Asn Glu Asp Gly Ser
1               5                   10                  15

<210> SEQ ID NO 17
<211> LENGTH: 16
<212> TYPE: PRT
<213> ORGANISM: Streptococcus salivarius

<400> SEQUENCE: 17

Asp Asp Gln Gln Trp Ser Gly Ser Ala Thr Val Asn Ser Asp Gly Ser
1               5                   10                  15

<210> SEQ ID NO 18
<211> LENGTH: 11
<212> TYPE: PRT
<213> ORGANISM: Bacillus amyloliquefaciens

<400> SEQUENCE: 18

Lys Ala Thr Phe Gly Pro Ser Phe Leu Met Asn
1               5                   10

<210> SEQ ID NO 19
<211> LENGTH: 11
<212> TYPE: PRT
<213> ORGANISM: Bacillus subtilis

<400> SEQUENCE: 19

Gln Ser Thr Phe Ala Pro Ser Phe Leu Leu Asn
1               5                   10

<210> SEQ ID NO 20
<211> LENGTH: 11
<212> TYPE: PRT
<213> ORGANISM: Streptococcus mutans

<400> SEQUENCE: 20

Asn Ser Thr Trp Ala Pro Ser Phe Leu Ile Gln
1               5                   10

```
<210> SEQ ID NO 21
<211> LENGTH: 11
<212> TYPE: PRT
<213> ORGANISM: Streptococcus salivarius

<400> SEQUENCE: 21

Lys Ser Thr Trp Ala Pro Ser Phe Leu Ile Lys
 1               5                  10

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:
      Illustrative motif
<221> NAME/KEY: MOD_RES
<222> LOCATION: (3)
<223> OTHER INFORMATION: any amino acid other than Pro

<400> SEQUENCE: 22

Leu Pro Xaa Thr Gly
 1               5

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 23
ctgataataa tggaaatgta tcac                                        24

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 24
catgatcata agtttggtag taatag                                      26

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 25
gtgatacatt tccattatta tcag                                        24

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 26
ctattactac caaacttatg atcatg                                      26

<210> SEQ ID NO 27
```

```
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 27
ccatggccat ggtagaacgc aaggaacata aaaaaatg                           38

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 28
agatctagat ctgttaaatc gacgtttgtt aatttctg                           38

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (6)
<223> OTHER INFORMATION: a, t, c or g
<221> NAME/KEY: modified_base
<222> LOCATION: (15)
<223> OTHER INFORMATION: a, t, c or g

<400> SEQUENCE: 29
gaygtntggg aywsntgggc c                                              21

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (3)
<223> OTHER INFORMATION: a, t, c or g
<221> NAME/KEY: modified_base
<222> LOCATION: (6)
<223> OTHER INFORMATION: a, t, c or g
<221> NAME/KEY: modified_base
<222> LOCATION: (9)
<223> OTHER INFORMATION: a, t, c or g
<221> NAME/KEY: modified_base
<222> LOCATION: (12)
<223> OTHER INFORMATION: a, t, c or g

<400> SEQUENCE: 30
gtngcnswnc cnswccayts ytg                                            23

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 31
gaatgtaggt ccaatttttg gc                                             22

<210> SEQ ID NO 32
<211> LENGTH: 22
```

<212> TYPE: DNA
<213> ORGANISM: Artificial Sequence
<220> FEATURE:
<223> OTHER INFORMATION: Description of Artificial Sequence: Primer

<400> SEQUENCE: 32
cctgtccgaa catcttgaac tg                                          22

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (6)
<223> OTHER INFORMATION: a, t, c or g
<221> NAME/KEY: modified_base
<222> LOCATION: (9)
<223> OTHER INFORMATION: a, t, c or g
<221> NAME/KEY: modified_base
<222> LOCATION: (12)
<223> OTHER INFORMATION: a, t, c or g
<221> NAME/KEY: modified_base
<222> LOCATION: (18)
<223> OTHER INFORMATION: a, t, c or g
<221> NAME/KEY: modified_base
<222> LOCATION: (21)
<223> OTHER INFORMATION: a, t, c or g

<400> SEQUENCE: 33
arraanswng gngcvmangt nsw                                         23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (9)
<223> OTHER INFORMATION: a, t, c or g
<221> NAME/KEY: modified_base
<222> LOCATION: (12)
<223> OTHER INFORMATION: a, t, c or g
<221> NAME/KEY: modified_base
<222> LOCATION: (15)
<223> OTHER INFORMATION: a, t, c or g
<221> NAME/KEY: modified_base
<222> LOCATION: (21)
<223> OTHER INFORMATION: a, t, c or g

<400> SEQUENCE: 34
tayaayggng tngcngargt naa                                         23

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 35
ccgaccatct tgtttgatta ac                                          22

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Primer -continued

```
<400> SEQUENCE: 36
aaytataayg gygttgcryg aagt                                           24

<210> SEQ ID NO 37
<211> LENGTH: 21
<212> TYPE: DNA
<213> ORGANISM: Artificial Sequence
<220> FEATURE:
<221> NAME/KEY: modified_base
<222> LOCATION: (6)
<223> OTHER INFORMATION: a, t, c or g
<221> NAME/KEY: modified_base
<222> LOCATION: (9)
<223> OTHER INFORMATION: a, t, c or g
<223> OTHER INFORMATION: Description of Artificial Sequence: Primer

<400> SEQUENCE: 37
taccgnwsnc tacttcaact t                                              21

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Consensus
      motif

<400> SEQUENCE: 38

Asn Glu Gln Lys
  1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Consensus
      motif

<400> SEQUENCE: 39

Asn His Gln Lys
  1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Consensus
      motif

<400> SEQUENCE: 40

Asn Asp Glu Gln
  1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Consensus
      motif

<400> SEQUENCE: 41

Gln His Arg Lys
  1
```

```
<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Consensus
      motif

<400> SEQUENCE: 42

Met Ile Leu Val
 1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Consensus
      motif

<400> SEQUENCE: 43

Met Ile Leu Phe
 1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Consensus
      motif

<400> SEQUENCE: 44

Ser Thr Asn Lys
 1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Consensus
      motif

<400> SEQUENCE: 45

Ser Thr Pro Ala
 1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Consensus
      motif

<400> SEQUENCE: 46

Ser Gly Asn Asp
 1

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Consensus
      motif
```

```
<400> SEQUENCE: 47

Ser Asn Asp Glu Gln Lys
  1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Consensus
      motif

<400> SEQUENCE: 48

Asn Asp Glu Gln His Lys
  1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Consensus
      motif

<400> SEQUENCE: 49

Asn Glu Gln His Arg Lys
  1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Consensus
      motif

<400> SEQUENCE: 50

Phe Val Leu Ile Met
  1               5
```

FRUCTOSYLTRANSFERASES

The present invention is in the field of enzymatic production of biomolecules. The invention is particularly concerned with two novel fructosyltransferases derived from lactobacilli and with a process for recombinant production of the enzymes and for the production of useful levans, in s and fructo-oligosaccharides from sucrose.

BACKGROUND OF THE INVENTION

Lactic acid bacteria (LAB) play an important role in the fermentative production of food and feed. Traditionally, these bacteria have been used for the production of for instance wine, beer, bread, cheese and yogurt and for the preservation of food and feed, e.g. olives, pickles, sausages, sauerkraut and silage, Because of these traditional applications, lactic acid bacteria are food-grade microorganisms that possess the Generally Recognised As Safe (GRAS) status. Due to the different products which are during fermentation with lactic acid bacteria, these bacteria contribute positively to the taste, smell and preservation of the final product. The group of lactic acid bacteria encloses several genera such as Lactobacillus, Leuconostoc, Pediococcus, Streptococcus, etc.

In recent years also the health promoting properties of lactic acid bacteria have received much attention. They produce an abundant variety of exopolysaccharides EPS's). These polysacharides are thought to contribute to human health by acting as prebiotic substrates, nutraceuticals, cholesterol lowering agents or immunomodulants.

To date high molecular weight polysaccharides produced by plants (such as cellulose, starch and pectin), seaweeds (such as alginate and carrageenan) and bacteria (such as algate, gellan and xanthan) are used in several industrial applications as viscosifying, stabilising, emulsifying, gelling or water binding agents. Although all these polysaccharides are used as food additives, they originate from organisms not having the GRAS status. Thus they are less desirable than the exopolysacciarides of microorganisms, such as lacic acid bacteria, which have the GRAS status.

The exopolysaccharides produced by LAB can be divided in two groups, heteropolysacchrides and homopolysaccharides; these are synthesized by totally different mechanisms. The former consist of repeating units in which residues of different types of sugars are present and the latter consist of one type of monosaccharide. The synthesis of heteropolysaccharides by lactic acid bacteria, including lactobacilli, has been studied extensively in recent years. Considerably less information is available on the synthesis of homopolysaccharides from lactobacilli, although some studies have been performed. Homopolysacoharides with fructose as the constituent sugar can be divided into two groups, inulins and levans. Inulins consist of 2,1-lined β-fructofuranoside residues, whereas levans consist of 2,6-linked β-fructofuranoside residues. Both can be linear or branched, The size of bacterial levans can vary from 20 kDa up to several MDa. There is limited information on the synthesis of levans, In most detail this synthesis has been studied in *Zymomonas mobilis* and in Bacillus species. Within lactic acid bacteria, fructosyltransferases have only been studied in streptococci. So far no fructosyltransferases have been reported in lactobacilli.

In a recent report the *Lactobacillus reuteri* strain LB 121 was found to produce both a glucan and a fructan when grown on sucrose, but only a fructan when grown on raffinose (van Geel-Schutten, G. H. et al., Appl. Microbiol. Biotechnol. (1998) 50, 697–703). In another report the glucan and fructan were characterize by their molecular weights (of 3,500 and 150 kDa respectively) and the glucan was reported to be highly branched with a unique structure consisting of a terminal, 4-substituted, 6-substituted, and 4,6-disubstituted β-glucose in a molar ratio 1.1:2.7:1.5:1.0 (van Geel-Schutten, G. H. et al., Appl. Environ. Microbiol. (1999) 65, 3008–3014). The fructan was identified as a linear (2→6)-β-D-fructofuranan (also called a levan). This was the first example of fructan synthesis by a Lactobacillus species.

SUMMARY OF THE INVENTION

Two novel genes encoding enzymes having fructosyltransferase activity have now been found in *Lactobacillus reuteri*, and their amino acid sequences have been determined. These are the first two enzymes identified in a Lactobacillus species capable of producing a fructan, One of the eves is an inulosucrase which produces a high molecular weight ($>10^7$ Da) fructan containing β(2-1) linked fructosyl units and fructo-oligosaccharides, while the other is a levansucrase which produces a fructan containing β(2-6) linked fructosyl units. The invention thus pertains to the enzymes, to DNA encoding them, to recombinant cells containing such DNA and to their use in producing carbohydrates, as defined in the appending claims.

DESCRIPTION OF THE INVENTION

It was found according to the invention that one of the novel fructosyltransferases (FTFA; an inulosucrase) produces a high molecular weight inulin with β(2-1) linked fructosyl units and fructo-oligosaccharides. The fructo-oligosaccharides synthesis was also observed in certain Lactobacillus strains, in particular in certain strains of *Lactobacillus reuteri*. However, the inulin has not been found in *Lactobacillus reuteri* culture supernatants, but only in extracts of *E. coli* cells expressing the above-mentioned fructosyltransferase. This inulosucrase consists of either 798 amino acids (2394 nucleotides) or 789 amino acids (2367 nucleotides) depending on the potential start codon used. The molecular weight (MW) deduced of the amino acid sequence of the latter form is 86 kDa and its isoelectric point is 4.51, at pH 7.

The amino acid sequence of the inulosucrase is shown in SEQ ID No. 1 (FIG. 1, amino acid residues 1–789). As mentioned above, the nucleotide sequence contains two putative start codons leading to either a 2394 or 2367 nucleotide form of the inulinsucrase. Both putative start codons are preceded by a putative ribosome binding site, GGGG (located 12 base pairs upstream its start codon) or AGGA (located 14 base pairs upstream its start codon), respectively (see FIG. 1).

The present invention covers a protein having inulosucrase activity with an amino acid identity of at least 65%, preferably at least 75%, and more preferably at least 85%, compared to the amino acid sequence of SEQ ID No. 1. The invention also covers a part of a protein with at least 15 contiguous amino acids which are identical to the corresponding part of the amino acid sequence of SEQ ID No. 1.

Fructosyltransferases have been found in several bacteria such as *Zymomonas mobilis, Erwinia amylovora, Acetobacter amylovora, Bacillus polymyxa, Bacillus amyloliquefaciens, Bacillus stearothermophilus*, and *Bacillus subtilis*. In lactic acid bacteria this type of enzyme previously has only been found in some streptococci. Most bacterial fructosyltransferases have a molecular mass of 50–100 kDa (with the exception of the fructosyltransferase found in *Streptococcus salivarius* which has a molecular mass of 140 kDa). Amino acid sequence alignment revealed that the novel inulosucrase of lactobacilli has high homology with fructosyltransferases originating from Gram positive bacteria, in particular with Streptococcus enzymes. The highest homology (FIG. 2) was found with the SacB enzyme of *Streptococcus mutans* Ingbritt A (62% identity within 539 amino acids).

Certain putative functions based on the alignment and site-directed mutagenesis studies can be ascribed to several amino acids of the novel inulosucrase, Asp-263, Glu-330, Asp-415, Glu-431, Asp-511, Glu-514, Arg-532 and/or Asp-551 of the amino acid sequence of SEQ ID No. 1 are identified as putative catalytic residues. Noteworthy, a hydrophobicity plot according to Kyte and Doolittle (1982) J. Mol. Biol. 157, 105–132 suggests that the novel inulosucrase contains a putative signal sequence according to the Von Heijne rule. The putative signal peptidase site is located between Gly at position 21 and Ala at position 22. Furthermore, it is striking that the C-terminal amino acid sequence of the novel inulosucrase contains a putative cell wall anchor amino acid signal LPXTG (SEQ ID NO: 22) and a 20-fold repeat of the motif PXX (see FIG. 1), where P is proline and X is any other amino acid. In 15 out of 20 repeats, however, the motif is PXT. This motif has so far not been reported in proteins of prokaryotic and eukaryotic origin.

A nucleotide sequence encoding any of the above mentioned proteins, mutants, variants or parts thereof is also a subject of the invention. Furthermore, the nucleic acid sequences corresponding to expression regulating regions (promoters, enhancers, terminators) of at least 30 contiguous nucleic acids contained in the nucleic acid sequence (-67)–(-1) or 2367–2525 of FIG. 1 can be used for homologous or heterologous expression of genes. Such expression-regulating sequences are operationally linked to a polypeptide-encoding nucleic acid sequence such as the genes of the fructosyltransferase according to the invention. A nucleic acid construct comprising the nucleotide sequence operationally linked to an expression-regulating nucleic acid sequence is also covered by the invention.

A recombinant host cell, such as a mammalian (with the exception of human), plant, animal, fungal or bacterial cell, containing one or more copies of the nucleic acid construct mentioned above is an additional subject of the invention. The inulosucrase gene (staring at nucleotide 41) has been cloned in an *E. coli* expression vector under the control of an ara promoter in *E. coli* Top10. *E. coli* Top10 cells expressing the recombinant inulosucrase hydrolysed sucrose and synthesized fructan material. SDS-PAGE of arabinose induced *E. coli* Top10 cell extracts suggested that the recombinant inulosucrase has a molecular weight of 80–100 kDa, which is in the range of other known fructosyltransferases and in line with the molecular weight of 86 kDa deduced of the amino acid sequence depicted in FIG. 1.

The invention further covers an inulosucrase according to the invention which, in the presence of sucrose, produces a inulin having β(2-1)-linked D-fructosyl units and fructo-oligosaccharides. Two different types of fructans, inulins and levans, exist in nature. Surprisingly, the novel inulosucrase expressed in *E. coli* Top10 cell synthesizes a high molecular weight (>$10^7$ Da) inulin and fructo-oligosaccharides, while in *Lactobacillus reuteri* culture supernatants, in addition to the fructo-oligosaccharides, a levan and not an inulin is found, This discrepancy can have several explanations: the inulosucrase gene may be silent in *Lactobacillus reuteri*, or may not be expressed in *Lactobacillus reuteri* under the conditions tested, or the inulosucrase may only synthesize fructo-oligosaccharides in its natural host, or the inulin polymer may be degraded shortly after synthesis, or may not be secreted and remains cell-associated, or the inulosucrase may have different activities in *Lactobacillus reuteri* and *E. coli* Top10 cells.

It was furthermore found according to the invention that certain lactobacilli, in particular *Lactobacillus reuteri*, possess another fructosyltransferase, a levansucrase (FTFB), in addition to the inulosucrase described above. The N-terminal amino acid sequence of the fructosyltransferase purified from *Lactobacillus reuteri* supernatant was found to be (portion of SEQ ID NO: 6) QVESNNYNGVAEVNTER-QANGQI. Furthermore, three internal sequences were identified, namely (SEQ ID NOS 7, 8 & 9, respectively in order of appearance) (M)(A)HLDVWDSWPVQDP(V), NAGSIFGT(K), V(E)(E)VYSPKVSTLMASDEVE. The N-terminal amino acid sequence could not be identified in the deduced inulosucrase sequence. Also the amino acid sequences of the three internal peptide fragments of the purified fructosyltransferase were not present in the putative inulosucrase sequence. Evidently, the inulosucrase gene does not encode the purified fructosyltransferase synthesizing the levan. The fructan produced by the levansucrase was identified in the *Lactobacillus reuteri* culture supernatant as a linear (2→6)-β-D-fructofuranan with a molecular weight of 150 kDa. The purified enzyme also produces this fructan.

Additionally, the invention thus covers a protein having levansucrase activity with an amino acid identity of at least 65%, preferably at least 75%, and more preferably at least 85%, compared to the amino acid sequence of SEQ ID NO. 2 (see FIG. 3). The second novel fructosyltransferase produces a high molecular weight fructan with β(2-6) linked fructosyl units with sucrose or raffinose as substrate. Furthermore, the invention covers a protein or a part thereof having levansucrase activity containing one or more of the three internal peptide fragments and/or the N-terminal amino acid sequence shown in SEQ ID No. 2 or a part thereof hang at least 7 contiguous amino acids, preferably at least 10 contiguous amino acids, more preferably at least 12 contiguous amino acids or even at least 15 contiguous amino acids, which are identical to the corresponding part of the amino acid sequence of SEQ ID No. 2. A nucleotide sequence encoding any of the above-mentioned proteins, mutants, variants or parts thereof is a subject of the invention as well as a nucleic acid construct comprising the nucleotide sequence mentioned above operationally linked to an expression-regulating nucleic acid sequence. A recombinant host cell, such as a mammalian (with the exception of human), plant, animal, fungal or bacterial cell, containing one or more copies of the nucleic acid construct mentioned above is an additional subject of the invention. The invention further covers a protein according to the invention which, in the presence of sucrose, produces a fructan having β(2-6)-linked D-fructosyl units.

The invention also pertains to a process of producing an inulin-type and/or a levan-type of fructan as described above using fructosyltransferases according to the invention and a suitable fructose source such as sucrose or raffinose. The fructans may either be produced by (Lactobacillus) strains containing one or both fructosyl transferases or by a fructosyltransferase enzyme isolated by conventional means from the culture of fructosyltransferases-positive lactobacilli, especially a *Lactobacillus reuteri*, or from a recombinant organism containing the fructosyltransferase gene or genes.

Additionally, the invention concerns a process of producing fructo-oligosaccharides containing the characteristic structure of the fructans described above using a Lactobacillus strain containing one or both fructosyltransferases or an isolated fructosyltransferase according to the invention. There is a growing interest in oligosaccharides derived from homopolysaccharides, for instance for prebiotic purposes. Several fructo- and gluco-oligosaccharides are known to stimulate the growth of bifidobacteria in the human colon. Fructo-oligosaccharides produced by the fructosyltransferase described above are also part of the invention. Another way of producing fructo-oligosaccharides is by hydrolysis of the fructans described above. This hydrolysis can be performed by known hydrolysis methods such as enzymatic hydrolysis with enzymes such as levanase or inulinase or by acid hydrolysis. The fructo-oligosaccharides to be produced according to the invention prefarably contain at least 2, more preferably at least 3, up to about 20 anhydrofructose units, optionally in addition to one or more other (glucose, galactose, etc.) units. These fructo-oligosaccharides are useful as prebiotics, and can be administered to a mammal in need of improving the bacterial status of the colon.

The invention also concerns chemically modified fructans and fructo-oligosaccharides based on the fructans described above. Chemical modification can be achieved by oxidation, such as hypochlorite oxidation resulting in ring-opened 2,3-dicarboxy-anhydrofictose units (see e.g. EP-A427349), periodate oxidation resulting in Ring-opened 3,4-dialdehyde-anhydrofructose units (see e.g. WO 95/12619), which can be further oxidised to (partly) carboxylated units (see e.g. WO 00/26257), TEMPO-mediated oxidation resulting in 1- or 6-carboxy-anhydrofructose units (see e.g. WO 95/07303). The oxidised fructans have improved water-solubility, altered viscosity and a retarded fermentability and can be used as metal-complexing agents, detergent additives, strengthening additives, bioactive carbohydrates, emulsifiers and water binding agents. They can also be used as starting materials for further derivatisation such as cross-lining and the introduction of hydrophobes. Oxidised fructans coupled to amino compounds such as proteins, or fatty acids can be used as emulsifiers and stabilizers. (Partial) hydrolysis of said fructans would result in fructo-oligosaccharides, which can be used as bioactive carbohydrates or prebiotics.

Another type of chemical modification is phosphorylation, as described in O. B. Wurzburg (1986) Modified Starches: properties and uses. CRC Press Inc., Boca Raton, 97–112. One way to achieve this modification is by dry heating fructan with a mixture of monosodium and disodium hydrogen phosphate or with tripolyphosphate. The phosphorzylated fructans are suitable as wet-end additives in papermaking, as binders in paper coating compositions, as warp sizing-agents, and as core binders for sand molds for metal casting. A further type of derivatisation of the fructans is acylation, especially. acetylation using acetic or propionic anhydride, resulting in products suitable as bleaching assistants and for the use in foils. Acylation with e.g. alkenyl succinic anhydrides or (activated) fatty acids results in surface-active products suitable as e.g. surfactants, emulsifiers, and stabilizers.

Hydroxyalkylation, carboxymethylation, and aminoalkylation are other methods of chemical derivatisation of the fructans. Hydroxyalkylation is commonly performed by base-catalysed reaction with alkylene oxides, such as ethylene oxide, propylene oxide or epichlorohydrine; the hydroxyalkylated products have improved solubility and viscosity characteristics. Carboxymethylation is achieved by reaction of the fructans with monochloroacetic acid or its alkali metal salts and results in anionic polymers suitable for various purposes including crystallisation inhibitors, and metal complexants. Amino-alkylation can be achieved by reaction of the fans with alkylene amines, haloalkyl amines or amino-alkylene oxides, or by reaction of epichlorohydrine adducts of the fructans with suitable amines. These products can be used as cationic polymers in a variety of applications, especially as a wet-end additive in paper making to increase strength, for filler and fines retention, and to improve the drainage rate of paper pulp. Other potential applications include textile sizing and wastewater purification. The above mentioned modifications can be used either separately or in combination depending on the desired product. Furthermore, the degree of chemical modification is variable and depends on the intended use. If necessary 100% modification, i.e. modification of all anhydrofructose units can be performed. However, partial modification, e.g. from 1 modified anhydrofructose unit per 100 up to higher levels, will often be sufficient in order to obtain the desired effect. The modified fructans have a DP (degree of to polymerisation) of at least 100, preferably at least 1000 units.

Use of a Lactobacillus strain capable of producing a levan, inulin or fructo-oligosaccharides or a mixture thereof as a probiotic, is also covered by the invention. Preferably, the Lactobacillus strain is also capable of producing a glucan, especially an 1,4/1,6-α-glucan as referred to above. The efficacy of some *Lactobacillus reuteri* strains as a probiotics has been demonstrated in various animals such as for instance poultry and humans. The admission of some Lactobacillus reuteri strains to pigs resulted in significantly lower serum total and LDL-cholesterol levels, while in children *Lactobacillus reuteri* is used as a therapeutic agent against acute diarrhea. For this and other reasons *Lactobacillus reuteri* stains, which were not reported to produce the glucans or fructans described herein, have been supplemented to commercially available probiotic products. The mode of action of *Lactobacillus reuteri* as a probiotic is still unclear. Preliminary studies indicated that gut colonization by *Lactobacillus reuteri* may be of importance. According to the invention, it was found that the mode of action of *Lactobacillus reuteri* as a probiotic may reside partly in the ability to produce polysaccharides. Lactobacillus strains, preferably *Lactobacillus reuteri* strains, and more preferably *Lactobacillus reuteri* strain LB 121 and other strains containing one or more fructosyltransferase genes encoding proteins capable of producing inulins, levans and/or fructo-oligosaccharides can thus advantageously be used as a probiotic. They can also, together with these polysaccharides, be used as a symbiotic.

EXAMPLES

Example 1

Isolation of DNA from *Lactobacillus reuteri* Nucleotide Sequence Analysis of the Inulosucrase (ftfA) Gene, Construction of Plasmids for Expression of the Inulosucrase Gene in *E. coli* Top10, Expression of the Inulosucrase Gene in *E. coli* Top10 and Identification of the Produced Polysaccharides Produced by the Recombinant Enzyme General procedures for cloning, DNA manipulations and agarose gel electrophoresis were essentially as described by Sambrook et al. (1989) Molecular cloning: a laboratory manual, 2nd ed. Cold Spring Harbour Laboratory Press, Cold Spring Harbour, N.Y. Restriction endonuclease digestions and ligations with T4 DNA ligase were performed as recommended by the suppliers. DNA was amplified by PCR techniques using ampliTAQ DNA polymerase (Perkin Elmer) or Pwo DNA polymerase. DNA fragments were isolated from agarose gels using the Qiagen extraction kit (Qiagen GMBH), following the instructions of the suppliers. *Lactobacillus reuteri* strain 121 (LMG 18388) was grown at 37° C. in MRS medium (DIFCO) or in MRS-s medium (MRS medium containing 100 g/l sucrose instead of 20 g/l glucose). When fructo-oligosaccharides production was investigated phosphate was omitted and ammonium citrate was replaced by ammonium nitrate in the MRS-s medium. *E. coli* sins were grown aerobically at 37° C. in LB medium, where appropriate supplemented with 50 µg/ml ampicillin (for selection of recombinant plasmids) or with 0.02% (w/v) arabinose (for induction of the inulosucrase gene).

Total DNA of *Lactobacillus reuteri* was isolated according to Verhasselt et al. (1989) FEMS Microbiol, Lett. 59, 135–140 as modified by Nagy et al (1995) J. Bacteriol. 177, 676–687.

The inulosucrase gene was identified by amplification of chromosomal DNA of *Lactobacillus reuteri* with PCR using degenerated primers (5ftf, 6ftfi, and 12ftfi, see table 1) based on conserved amino acid sequences deduced from different bacterial fructosyltransferase genes (SacB of *Bacillus amyloliquefaciens*, SacB of *Bacillus subtilis, Streptococcus mutans* fructosyltransferase and *Streptococcus salivarius* fructosyltransferase, see FIG. 4) and *Lactobacillus reuteri* DNA as template. Using primers 5ftf and 6ftfi, an amplification product with the predicted size of about 234 bp was obtained (FIG. 5A). This 234 bp fragment was cloned in *E. coli* JM109 using the pCR2.1 vector and sequenced. Transformations were performed by electroporation using the BioRad gene pulser apparatus at 2.5 kV, 25 µF and 200 Ω, following the instructions of the manufacturer. Sequencing was performed according to the method of Sanger et al (1977) Proc. Natl. Acad. Sci. USA 74, 5463–5467. Analysis of the obtained sequence data confirmed that part of a fructosyltransferase (ftf) gene had been isolated. The 234 bp amplified fragment was used to design primers 7ftf and 8ftfi (see table 1). PCR with the primers 7ftf and 12ftfi gave a product of the predicted size of 948 bp (see FIG. 5B); its sequence showed clear similarity with previously characterized fructosyltransferase genes. The 948 bp amplified fragment was used to design the primers ftfAC1(i) and ftfAC2(i) (see table 1) for inverse PCR. Using inverse PCR techniques a 1438 bp fragment of the inulosucrase gene was generated, including the 3' end of the inulosucrase gene (see FIG. 5C). The remaining 5' fragment of the inulosucrase gene was isolated with a combination of standard and inverse PCR techniques. Briefly, *Lactobacillus reuteri* DNA was cut with restriction enzyme XhoI and ligated. PCR with the primers 7ftf and 8ftfi, using the ligation product as a template, yielded a 290 bp PCR product which was cloned into pCR2.1 and sequenced. This revealed that primer 8ftfi had annealed a specifically as well as specifically yielding the 290 bp product (see FIG. 5D).

At this time, the N-terminal amino acid sequence of a fructosyltransferase enzyme (FTFB) purified from the *Lactobacillus reuteri* strain 121 was obtained. This sequence consisted of the following 23 amino acids: (portion of SEQ ID NO: 6) QVESNNYNGVAEVNTERQANGQI (see FIG. 1 and SEQ ID No. 2 in FIG. 3). The degenerated primer 19ftf (portion of SEQ ID NO: 6) (YNGVAEV) was designed on the basis of a part of this N-terminal peptide sequence and primer 20ftfi was designed on the 290 bp PCT product. PCR with primers 19ftf and 20ftfi gave a 754 bp PCT product (see FIG. 5E), which was cloned into pCR2.1 and sequenced. Both DNA strands of the entire fructosyltransferase gene were double sequenced. In this way the sequence of a 2.6 kb region of the *Lactobacillus reuteri* DNA, containing the inulosucrase gene and its surroundings were obtained.

The plasmids for expression of the inulosucrase gene in *E. coli* Top10 were constructed as described hereafter. A 2414 bp fragment, containing the inulosucrase gene starting at the first putative start codon at position 41, was generated by PCR, using primers ftfA1 and ftfA2i. Both primers contained suitable restriction enzyme recognition sites (a NcoI site at the 5' end of ftfA1 and a BglII site at the 3' end of ftfA2i). PCR with *Lactobacillus reuteri* DNA, Pwo DNA polymerase and primers ftfA1and ftfA2i yielded the complete inulosucrase gene flanked by NcoI and BglII restriction sites. The PCR product with blunt ends was ligated directly into pCRbluntII-Topo. Using the NcoI and BglII restriction sites, the putative ftfA gene was cloned into the expression vector pBAD, downstream of the inducible arabinose promoter and in frame upstream of the Myc epitope and the His tag. The pBAD vector containing the inulosucrase gene (pSVH101) was transformed to *E. coli* Top10 and used to study inulosucrase expression. Corrects construction of plasmid containing the complete inulosucrase gene was confirmed by restriction enzyme digestion analysis and by sequence analysis, showing an in frame cloning of the inulosucrase gene using the ribosomal binding site provided by the pBAD vector and the first putative start codon (at position 41) of inulosucrase (see FIG. 1).

Plasmid DNA of *E. coli* was isolated using the alkaline lysis method of Bimboim and Doly (1979) Nucleic Acids Res. 7, 1513–1523 or with a Qiagen plasmid kit following the instructions of the supplier. Cells of *E. coli* Top10 with pSVH101 were grown overnight in LB medium containing 0.02% (w/v) arabinose and were harvested by centrifugation. The pellet was washed with 25 mM sodium acetate buffer pH 5.4 and the suspension was centrifuged again. Pelleted cells were resuspended in 25 mM sodium acetate buffer pH 5.4. Cells were broken by sonication. Cell debris and intact cells were removed by centrifugation for 30 min at 4° C. at 10,000×g and the resulting cell free extract was used in the enzyme assays.

The fructosyltransferase activities were determined at 37° C. in reaction buffer (25 mM sodium acetate, pH 5.4, 1 mM $CaCl_2$, 100 g/l sucrose) by monitoring the release of glucose from sucrose, by detecting fructo-oligosaccharides or by determining the amount of fructan polymer produced using *E. coli* cell free extracts or *Lactobacillus reuteri* culture supernatant as enzyme source. Sucrose, glucose and fructose were determined enzymatically using commercially available kits.

Fructan production by *Lactobacillus reuteri* was studied with cells grown in MRS-s medium. Product formation was also studied with cell-free extracts of *E. coli* containing the novel inulosucrase incubated in reaction buffer (1 mg protein/10 ml buffer, incubated overnight at 37° C.). Fructans were collected by precipitation with ethanol. $^1$H-NMR spectroscopy and methylation analysis were performed as described by van Geel-Schutten et al. (1999) Appl. Environ. Microbiol. 65, 3008–3014. The molecular weights of the fructans were determined by high performance size exclusion chromatography coupled on-line with a multi angle laser light scattering and a differential refractive index detector. Fructo-oligosaccharides synthesis was studied in

9

*Lactobacillus reuteri* culture supernatants and in extracts of *E. coli* cells containing the novel inulosucrase incubated in reaction buffer (1 mg protein/10 ml buffer, incubated overnight at 37° C.). Glucose and fructose were determined enzymatically as described above and fructo-oligosaccharides produced were analyzed using a Dionex column. The incubation mixtures were centrifuged for 30 min at 10,000×g and diluted 1:5 in a 100% DMSO solution prior to injection on a Dionex column. A digest of inulin (DP1-20) was used as a standard. Separation of compounds was achieved with anion-exchange chromatography on a CarboPac PA1 column (Dionex) coupled to a CarboPac PA1 guard column (Dionex). Using a Dionex GP50 pump the following gradient was generated: % eluent B is 5% (0 min); 35% (10 min); 45% (20 min); 65% (50 min); 100% (54–60 min); 5% (61–65 min). Eluent A was 0.1 M NaOH and eluent B was 0.6 M NaAc in a 0.1 M NaOH solution. Compounds were detected using a Dionex ED40 electrochemical detector with an AU working electrode and a Ag/AgCl reference-electrode with a sensitivity of 300 nC. The pulse program used was:+0.1 Volt (0–0.4 s); +0.7 Volt (0.41–0.60 s); −0.1 Volt (0.61–1.00 s). Data were integrated using a Perkin Elmer Turbochrom data integration system. A different separation of compounds was done on a cation exchange column in the calcium form (Benson BCX4). As mobile phase Ca-EDTA in water (100 ppm) was used, The elution speed was 0.4 ml/mini at a column temperature of 85° C. Detection of compounds was done by a refractive index (Jasco 830-RI) at 40° C. Quantification of compounds was achieved by using the software program Turbochrom (Perkin Elmer).

SDS-PAGE was performed according to Laemmli (1970) Nature 227, 680–685 using 7.5% polyacrylamide gels. After electrophoresis gels were stained with Coomassie Briljant Blue or an activity staining (Periodic Acid Schiff, PAS) was carried out as described by Van Geel-Schutten et al (1999) Appl. Environ. Microbiol. 65, 3008–3014.

TABLE 1

Nucleotide sequence of primers used in PCR reactions to identify the inulosucrase gene.

| Primer name | Location (bp) | Nucleotide sequence |
|---|---|---|
| ftfAC1 | 1176 | CTG-ATA-ATA-ATG-GAA-ATG-TAT-CAC |
| ftfAC2i | 1243 | CAT-GAT-CAT-AAG-TTT-GGT-AGT-AAT-AG |
| ftfac1 | 1176 | GTG-ATA-CAT-TTC-CAT-TAT-TAT-CAG |
| ftfAC2 | 1243 | CTA-TTA-CTA-CCA-AAC-TTA-TGA-TCA-TG |
| ftfA1 |  | CCA-TGG-CCA-TGG-TAG-AAC-GCA-AGG-AAC-ATA-AAA-AAA-TG |
| ftfA2i |  | AGA-TCT-AGA-TCT-GTT-AAA-TCG-ACG-TTT-GTT-AAT-TTC-TG |
| 5ftf | 845 | GAY-GTN-TGG-GAY-WSN-TGG-GCC |
| 6ftfi | 1052 | GTN-GCN-SWN-CCN-SWC-CAY-TSY-TG |
| 7ftf | 1009 | GAA-TGT-AGG-TCC-AAT-TTT-TGG-C |
| 8ftfi | 864 | CCT-GTC-CGA-ACA-TCT-TGA-ACT-G |
| 12ftfi | 1934 | ARR-AAN-SWN-GGN-GCV-MAN-GTN-SW |
| 19ftf | 1 | TAY-AAY-GGN-GTN-GCN-GAR-GTN-AA |
| 20ftfi | 733 | CCG-ACC-ATC-TTG-TTT-GAT-TAA-C |

Listed from left to right are: primer name (i, inverse primer), location (in bp) in ftfA and the sequence from 5' to 3' according to IUB group codes (N = any base; M = A or C; R = A or G; W = A or T; S = C or G; Y = C or T; K = G or T; B = not A; D = not C; H = not G; and V = not T).

10

Example 2

Purification and Amino Acid Sequencing of the Levansucrase (FTFB)

Protein Purification

Samples were taken between each step of the purification process to determine the enzyme activity (by glucose GOD-Perid method) and protein content (by Bradford analysis and acrylamide gel electrophoresis). Collected chromatography fractions were screened for glucose liberating activity (GOD-Perid method) to determine the enzyme activity.

One liter of an overnight culture of LB121 cells grown on MRS medium containing 50 grams per liter maltose was centrifuged for 15 min. at 10,000×g. The supernatant was precipitated with 1.5 liter of a saturated ammonium sulphate solution. The ammonium sulphate solution was added at a rate of 50 ml/min. under continuous stirring. The resulting 60% (w/v) ammonium sulphate solution was centrifuged for 15 min. at 10,000×g. The precipitate was resuspended in 10 ml of a sodium phosphate solution (10 mM, pH 6.0) and dialysed overnight against 10 mM sodium phosphate, pH 6.0.

A hydroxylapatite column was washed with a 10 mM sodium phosphate solution pH 6.0; the dialysed sample was loaded on the column, After eluting the column with 200 mM sodium phosphate, pH 6.0 the eluted fractions were screened for glucose releasing activity and fractions were pooled for phenyl superose (a hydrophobic interactions column) chromatography.

The pooled fractions were diluted 1:1 (v:v) with 25 mM sodium acetate, 2 M ammonium sulphate, pH 5.4 and loaded on a phenyl superose column (washed with 25 mM sodium acetate, 1 M ammonium sulphate, pH 5.4). In a gradient from 25 mM sodium acetate, 1 M ammonium sulphate, pH 5.4 (A) to 25 mM sodium acetate, pH 5.4 (B) fractions were collected from 35% B to 50% B.

Pooled factions from the phenyl superose column were loaded on a gel filtration (superdex) column and eluted by a 25 mM acetate, 0.1 M sodium chloride, pH 5,4 buffer. The superdex fractions were loaded on a washed (with 25 mM sodium acetate, pH 5.4) Mono Q column and eluted with 25 mM sodium acetate, 1 M sodium chloride, pH 5,4. The fractions containing glucose liberating activity were pooled, dialysed at 25 mM sodium acetate, pH 5.4, and stored at −20° C.

A levansucrase enzyme was purified from LB121 cultures grown on media containing maltose using ammonium sulfite precipitation and several chromatography column steps (table 2). Maltose (glucose-glucose) was chosen because both glucansucrase and levansucrase can not use maltose as substrate. LB121 will grow on media containing maltose but will not produce polysaccharide. From earlier experiments it was clear at even with harsh methods the levansucrase enzyme could not be separated from its product levan. These harsh methods included boiling the levan in a SDS solution and treating the levan with HCl and TFA. No levanase enzyme was commercially available for the enzymatic breakdown of levanase. Only a single levansucrase was detected in maltose culture supernatants. In order to prove that the enzyme purified from maltose culture supernatant is the same enzyme which is responsible for the levan production during growth on raffinose, biochemical and biophysical tests were performed.

TABLE 2

Purification of the *Lactobacillus reuteri* LB 121 levansucrase (FTFB) enzyme.

| Step | Protein (mg) | Activity (U) | Total Activity (U/mg) | Specific (fold) | Purification (%) | Yield |
|---|---|---|---|---|---|---|
| Supernatant | 128 | 64 | 0.5 | 1 | 100 | |
| Ammonium sulfate precipitation (65%) | 35.2 | 42 | 12 | 2.4 | 65.6 | |
| Hydroxyl apatite | 1.5 | 30.6 | 20.4 | 40.8 | 47.8 | |
| Phenyl superose | 0.27 | 23 | 85 | 170 | 36 | |
| Gel Filtration | 0.055 | 10 | 182 | 360 | 16 | |
| MonoQ | 0.0255 | 4 | 176 | 352 | 6 | |

Amino Acid Sequencing of FTFB

A 5% SDS-PAA get was allowed to "age" overnight in order to reduce the amount of reacting chemical groups in the gel. Reaction of chemicals in the PAA gel (TEMED and ammonium persulphate) with proteins can cause some undesired effects, such as N-terminal blocking of the protein, making it more difficult to determine the protein amino acid composition. 0.1 mM thioglycolic acid (scavenger to reduce the amount of reactive groups in the PAA gel material) was added to the running buffer during electrophoresis.

In order to determine the amino acid sequence of internal peptides of protein bands running in a SDS-PAA gel, protein containing bands were cut out of the PAA gel. After fractionating the protein by digestion with chymotrpsin the N-terminal amino acid sequences of the digested proteins were determined (below).

N-terminal sequencing was performed by Western blotting of the proteins from the PAA gel to an Immobilon PVDF membrane (Milipore/ Waters Inc.) at 0.8 mA/cm$^2$ for 1 h. After staining the PVDF membrane with Coomassie Brilliant Blue without adding acetic acid (to reduce N-terminal blocking) and destaining with 50% methanol, the corresponding bands were cut out of the PVDF membrane for N-terminal amino acid sequence determination.

Amino acid sequence determination was performed by automated Edman degradation as described by Koningsberg and Steinman (1977) The proteins (third edition) volume 3, 1–178 (Neurath and Hill, eds.). The automated equipment for Edman degradation was an Applied Biosystems model 477A pulse-liquid sequenator described by Hewick et al (1981), J. Biol. Chem. 15, 7990–7997 connected to a RP-HPLC unit (model 120A, Applied Biosystems) for amino acid identification.

The N-terminal sequence of the purified FTFB was determined and found to be: (SEQ ID NO: 6) (A)QVESNNYNGVAEVNTERQANGQI(G)(V)(D). Three internal peptide sequences of the purified FTFB were determined: (SEQ ID NOS 7, 8 & 9, respectively in order of appearance) (M)(A)HLDVWDSWPVQDP(V); NAGSIFGT (K); and V(E)(E)VYSPKVSTLMASDEVE.

The following primers were designed on the basis of the N-terminal and internal peptide fragments of FTFB. Listed from left to right are: primer name, source peptide fragment and sequence (from 5' to 3'). FTFB1+FTFB3i yields approximately a 1400 bp product in a PCR reaction. FTFB1 forward (N-terminal): (SEQ ID NO: 36) AA T/C-TAT-AA T/C-GG T/C-GTT-GC G/A T/C-GAA-GT; and FTFB3i reverse (Internal 3): (SEQ ID NO: 37) TAC-CGN-A/T C/G N-CTA-CTT-CAA-CTT. The FTFB gene was partly isolated by PCR with primers FTFB1 and FTFB3i. PCR with these primers yielded a 1385 bp amplicon (see FIG. 3, SEQ ID No.

2), which after sequencing showed high homology to ftfA and SacB from *Streptococcus mutans*.

DESCRIPTION OF THE FIGURES

FIGS. 1(1)–1(4): SEQ ID NOS 1 & 3–5; The deduced amino acid sequence of the novel inulosucrase of *Lactobacillus reuteri* (amino acid 1–789). Furthermore, the designations and orientation (< for 3' to 5' and > for 5' to 3') of the primers and the restriction enzymes used for (inverse) PCR, are shown at the right hand side. Putative start codons (ATG, at positions 41 and 68) and stop codon (TAA, at position 2435) are shown in bold. The positions of the primers used for PCR are shown in bold/underlined. The NheI restriction sites (at positions 1154 and 2592) used for inverse PCR are underlined. The primers used and their exact positions in the inulosucrase sequence are shown in table 1. Starting at amino acid 690, the 20 PXX repeats are underlined. At amino acid 755 the LPXTG (SEQ ID NO: 22) motif is underlined.

FIG. 2: Dendrogram of bacterial and plant fructosyltransferases The horizontal distances are a measure for the difference at the amino acid sequence level. 10% difference is indicated by the upper bar. Bootstrap values (in percentages) are given at the root of each tree. Fructosyltransferases of Gram positive bacteria are indicated in the lower half of the figure (*B. staerothermophilus* SurB; *B. amylolIquefaciens* SacB; *B. subtilis* SacB; *S. mutans* SacB; *L. reuteri* FtfA (inulosucrase); *S. Salivarius* Ftf). Plant fructosyltransferases are indicated in the middle part of the figure (*Cynara scolymus* Ss-Ift; *Allium cepa* F-6gfi; *Hordeum vulgare* Sf-6ft). Fructosylbsferases of Gram negative bacteria are shown in the upper part of the figure (*Z. mobilis* LevU; *Z. mobilis* SucE2; *Z. mobilis* SacB; *E. amylovora* Les; *A. diazotrophicus*LsdA).

FIGS. 3(1) and 3(2) SEQ ID No. 2; The nucleotide sequence of a part of the novel levansucrase of *Lactobacillus reuteri* and the N-terminal (SEQ ID NO: 6) and three internal amino acid sequences of *Lactobacillus reuteri* (SEQ ID NOS 7–9).

FIG. 4: Parts of an alignment of the deduced amino acid sequences of some bacterial fructosyltransferase genes. Sequences in bold indicate the consensus sequences (SEQ ID NOS 10–21, respectively in order of appearance) used to construct the degenerated primers 5ftf, 6ftfi and 12 ftfi. (*) indicates a position with a fully conserved amino acid residue, (;) indicates a position with a fully conserved 'strong' group: STA, NEQK (SEQ ID NO: 38), NHQK (SEQ ID NO: 39), NDEQ (SEQ ID NO: 40), QHRK (SEQ ID NO: 41), MILV (SEQ ID NO: 42), MILF (SEQ ID NO: 43), HY, FYW, (,) indicates a position with a fully conserved 'weaker' group: CSA, ATV, SAG, STNK (SEQ ID NO: 44), STPA (SEQ ID NO: 45), SGND (SEQ ID NO: 46), SNDEQK (SEQ ID NO: 47), NDEQHK (SEQ ID NO: 48), NEQHRK (SEQ ID NO: 49), FVLIM (SEQ ID NO: 50), HFY. Groups are according to the Pam250 residue weight matrix described by Altschul et al. (1990) J. Mol. Biol. 215, 403–410.

FIG. 5: The strategy used for the isolation of the inulosucrase gene from *Lactobacillus reuteri* 121 chromosomal DNA.

We claim:

1. An isolated protein having inulosucrase activity, exhibiting at least 85% amino acid identity, as determined by a BLAST algorithm, with the amino acid sequence of SEQ ID No. 1.

2. The protein according to claim 1, comprising one or more of the amino acids Asp-263, Glu-330, Asp-415, Glu-431, Asp-511, Glu-514, Arg-532 and Asp-551 of the amino acid sequence of SEQ ID No. 1.

3. The protein according to claim 1, comprising an amino acid sequence Asp-263 to Asp-551 of the amino acid sequence of SEQ ID No. 1.

4. The protein according to claim 1, which is a recombinant protein.

5. A process for producing an inulosucrase, comprising culturing a Lactobacillus strain containing inulosucrase, according to claim 1 in a culture medium, and recovering the protein from a culture medium or a cell lysate.

* * * * *